US011180436B2

United States Patent
Liao et al.

(10) Patent No.: US 11,180,436 B2
(45) Date of Patent: Nov. 23, 2021

(54) METHOD FOR PURIFYING BY-PRODUCT ETHYLENE GLYCOL OF POLYESTER IN CONVERTING PLASTICIZER

(71) Applicant: NAN YA PLASTICS CORPORATION, Taipei (TW)

(72) Inventors: Te-Chao Liao, Taipei (TW); Jung-Jen Chuang, Taipei (TW); Chung-Yu Chen, Taipei (TW); Chiou-Nan Lai, Taipei (TW)

(73) Assignee: NAN YA PLASTICS CORPORATION, Taipei (TW)

( * ) Notice: Subject to any disclaimer, the term of this patent is extended or adjusted under 35 U.S.C. 154(b) by 0 days.

(21) Appl. No.: 16/892,359

(22) Filed: Jun. 4, 2020

(65) Prior Publication Data
US 2021/0087130 A1    Mar. 25, 2021

(30) Foreign Application Priority Data
Sep. 25, 2019  (TW) ................................. 108134578

(51) Int. Cl.
   *C07C 29/86* (2006.01)
   *C07C 29/80* (2006.01)
   *C07C 31/20* (2006.01)

(52) U.S. Cl.
   CPC .............. *C07C 29/86* (2013.01); *C07C 29/80* (2013.01); *C07C 31/202* (2013.01)

(58) Field of Classification Search
   CPC .................................. C07C 29/86; C07C 29/80
   See application file for complete search history.

(56) References Cited

U.S. PATENT DOCUMENTS

2012/0184783 A1 * 7/2012 Barnicki .............. B01J 31/2409
568/868

FOREIGN PATENT DOCUMENTS

| CN | 101569800 A  |   | 11/2009 |   |          |
|----|--------------|---|---------|---|----------|
| CN | 103044257 A  | * | 4/2013  |   | C07C 67/03 |
| CN | 103044257 A  |   | 4/2013  |   |          |
| CN | 103772148    | * | 5/2014  |   | C07C 29/86 |
| CN | 104370696    | * | 2/2015  |   | C07C 29/76 |
| CN | 105936620 A  |   | 9/2016  |   |          |
| CN | 110878007    | * | 3/2020  |   |          |
| WO | WO-2013148505 A1 | * | 10/2013 | | C07C 29/86 |

* cited by examiner

*Primary Examiner* — Rosalynd A Keys
(74) *Attorney, Agent, or Firm* — Li & Cai Intellectual Property (USA) Office

(57) ABSTRACT

A method for purifying by-product ethylene glycol of polyester in converting plasticizer includes: inputting a reaction liquid waste stream including ethylene glycol and 2-ethylhexanol into an ethylene glycol dehydration tower; inputting a hot water stream into the ethylene glycol dehydration tower to mix with the reaction liquid waste stream and to remove the 2-ethylhexanol from the reaction liquid waste stream; dehydrating the ethylene glycol via the ethylene glycol dehydration tower to collect a crude ethylene glycol stream including dehydrated ethylene glycol from a tower bottom of the ethylene glycol dehydration tower and to collect an organic liquid waste stream including the 2-ethylhexanol from a tower top of the ethylene glycol dehydration tower; and inputting the crude ethylene glycol stream into an ethylene glycol distillation tower to collect a ethylene glycol solution from a tower top of the ethylene glycol distillation tower.

9 Claims, 2 Drawing Sheets

METHOD FOR PURIFYING BY-PRODUCT ETHYLENE GLYCOL OF POLYESTER IN CONVERTING PLASTICIZER

CROSS-REFERENCE TO RELATED PATENT APPLICATION

This application claims the benefit of priority to Taiwan Patent Application No. 108134578, filed on Sep. 25, 2019. The entire content of the above identified application is incorporated herein by reference.

Some references, which may include patents, patent applications and various publications, may be cited and discussed in the description of this disclosure. The citation and/or discussion of such references is provided merely to clarify the description of the present disclosure and is not an admission that any such reference is "prior art" to the disclosure described herein. All references cited and discussed in this specification are incorporated herein by reference in their entireties and to the same extent as if each reference was individually incorporated by reference.

FIELD OF THE DISCLOSURE

The present disclosure relates to a method for purifying ethylene glycol, and more particularly to a method for purifying by-product ethylene glycol of polyester in converting plasticizer.

BACKGROUND OF THE DISCLOSURE

Generally, polyester waste (e.g., polyethylene terephthalate, PET) and raw material 2-ethylhexanol (2-EH) can react with each other to produce plasticizer (e.g., dioctyl terephthalate, DOTP) through a one-step method that combines alcoholysis and transesterification under the action of catalyst. The chemical reaction of the process will generate by-product ethylene glycol. However, the by-product ethylene glycol and the raw material 2-ethylhexanol are azeotropic and difficult to be separated from each other. Accordingly, in the synthesis step of the process, the ethylene glycol can be distilled from the 2-ethylhexanol using a water extraction reaction to produce a reaction liquid waste stream that includes the by-product ethylene glycol and trace amounts of the raw material 2-ethylhexanol.

However, most of the current research on the above process focuses on the choice of catalyst or the removal of ethylene glycol, but few studies focus on the recovery and purification of the by-product ethylene glycol.

Although the ethylene glycol can be recovered, the conventional method for recovering the ethylene glycol is to remove water in the reaction liquid waste stream by evaporation to improve the purity of ethylene glycol and accordingly recover the ethylene glycol. However, since the ethylene glycol and the 2-ethylhexanol are azeotropic and difficult to be separated from each other, the purity of ethylene glycol recovered by the conventional method is not high, and the recovered ethylene glycol is difficult to be used as raw material for producing other products, such as raw material for synthetic polyester.

China Patent Publication No. 105936620 proposes a purification device capable of purifying ethylene glycol in the preparation of plasticizer DOTP. The device uses the residual heat of ethylene glycol and 2-ethylhexanol generated by the reaction to heat and distill the separated ethylene glycol solution to save energy, but fails to solve the problem of low purity of ethylene glycol.

SUMMARY OF THE DISCLOSURE

In response to the above-referenced technical inadequacies, the present disclosure provides a method for purifying by-product ethylene glycol of polyester in converting plasticizer.

In one aspect, the present disclosure provides a method for purifying by-product ethylene glycol of polyester in converting plasticizer, which is a continuous collection method and comprises the following steps (1) to (4): (1) inputting a reaction liquid waste stream into an ethylene glycol dehydration tower; in which the reaction liquid waste stream includes ethylene glycol and 2-ethylhexanol; (2) inputting a hot water stream into the ethylene glycol dehydration tower to mix with the reaction liquid waste stream and to remove the 2-ethylhexanol from the reaction liquid waste stream so that the ethylene glycol is separated from the 2-ethylhexanol; in which the hot water stream is heated water, and a temperature of the hot water stream is between 40° C. and 95° C.; (3) dehydrating the ethylene glycol via the ethylene glycol dehydration tower to collect a crude ethylene glycol stream from a tower bottom of the ethylene glycol dehydration tower and to collect an organic liquid waste stream from a tower top of the ethylene glycol dehydration tower; in which the crude ethylene glycol stream includes the ethylene glycol that is dehydrated, and the organic liquid waste stream includes the 2-ethylhexanol; and (4) inputting the crude ethylene glycol stream into an ethylene glycol distillation tower to collect an ethylene glycol solution from a tower top of the ethylene glycol distillation tower.

Preferably, in the step (2), the temperature of the hot water stream is between 50° C. and 80° C.

Preferably, in the step (2), the hot water stream is inputted into a lower half portion of the ethylene glycol dehydration tower.

Preferably, in the step (3), the organic liquid waste stream collected from the tower top of the ethylene glycol dehydration tower has a COD value of not greater than 1,200 mg/L.

Preferably, in the step (4), the ethylene glycol solution collected from the tower top of the ethylene glycol distillation tower has an ethylene glycol purity of not less than 90%.

Preferably, the step (4) further includes: collecting a high boiling point mixture from a tower bottom of the ethylene glycol distillation tower.

Preferably, in the step (4), the high boiling point mixture collected from the tower bottom of the ethylene glycol distillation tower has a calorific value of not less than 1,500 kcal/kg.

Preferably, the tower bottom of the ethylene glycol dehydration tower is heated by a reboiler loop to provide the heat required for distillation, and the heat source of the reboiler loop is high pressure steam.

Preferably, a pressure at the tower top of the ethylene glycol dehydration tower is not greater than 1 bar, a reflux ratio of the ethylene glycol dehydration tower is between 0.01 and 3, a temperature at the tower top of the ethylene glycol dehydration tower is between 50° C. and 100° C., and a temperature at the tower bottom of the ethylene glycol dehydration tower is between 80° C. and 160° C.

Preferably, a pressure at the tower top of the ethylene glycol distillation tower is not greater than 1 bar, a reflux ratio of the ethylene glycol distillation tower is between 0.01 and 10, a temperature at the tower top of the ethylene glycol distillation tower is between 120° C. and 150° C., and a temperature at the tower bottom of the ethylene glycol distillation tower is between 130° C. and 170° C.

Preferably, the reaction liquid waste stream has a mass flow rate between 300 kg/h and 1,200 kg/h when being inputted into the ethylene glycol dehydration tower, and the hot water stream has a mass flow rate between 30 kg/h and 600 kg/h when being inputted into the ethylene glycol dehydration tower.

Preferably, a mass flow ratio of the reaction liquid waste stream to the hot water stream is between 1:0.1 and 1:0.5.

Therefore, by virtue of "(2) inputting a hot water stream into the ethylene glycol dehydration tower to mix with the reaction liquid waste stream and to remove the 2-ethylhexanol from the reaction liquid waste stream so that the ethylene glycol is separated from the 2-ethylhexanol; in which the hot water stream is heated water, and a temperature of the hot water stream is between 40° C. and 95° C.", "(3) dehydrating the ethylene glycol via the ethylene glycol dehydration tower to collect a crude ethylene glycol stream from a tower bottom of the ethylene glycol dehydration tower and to collect an organic liquid waste stream from a tower top of the ethylene glycol dehydration tower; in which the crude ethylene glycol stream includes the ethylene glycol that is dehydrated, and the organic liquid waste stream includes the 2-ethylhexanol", and "(4) inputting the crude ethylene glycol stream into an ethylene glycol distillation tower to collect an ethylene glycol solution from a tower top of the ethylene glycol distillation tower", the recovered ethylene glycol solution has high purity, and thus has high application value. Moreover, the waste (e.g., organic liquid waste stream or high boiling point mixture) generated in the method of the present disclosure can be directly treated by wastewater treatment or incineration, which will not cause serious pollution to the environment.

These and other aspects of the present disclosure will become apparent from the following description of the embodiment taken in conjunction with the following drawings and their captions, although variations and modifications therein may be affected without departing from the spirit and scope of the novel concepts of the disclosure.

BRIEF DESCRIPTION OF THE DRAWINGS

The present disclosure will become more fully understood from the following detailed description and accompanying drawings.

DETAILED DESCRIPTION OF THE EXEMPLARY EMBODIMENTS

Figure 1:
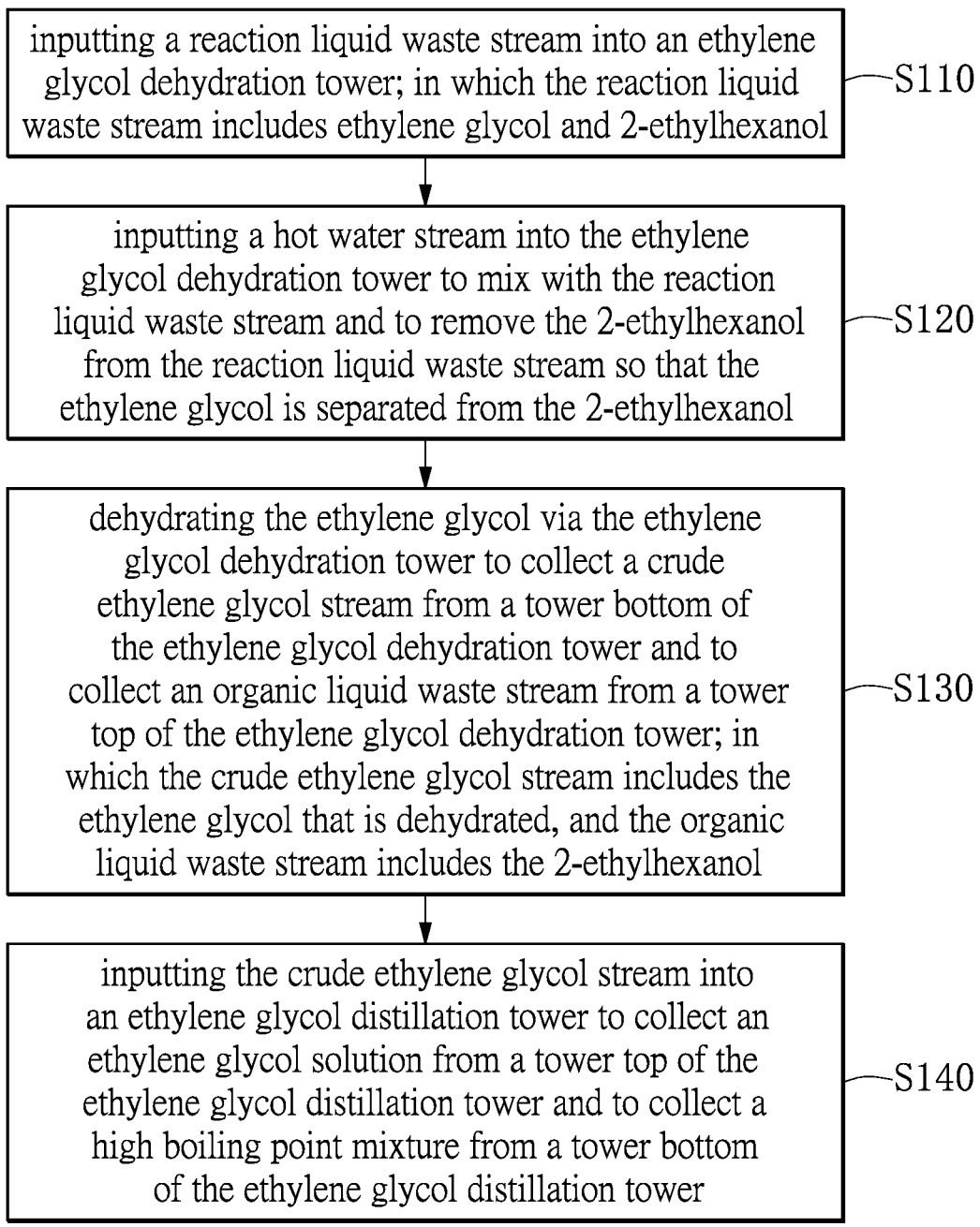
FIG. 1 is a flowchart of a method for purifying ethylene glycol according to an embodiment of the present disclosure.

The present disclosure is more particularly described in the following examples that are intended as illustrative only since numerous modifications and variations therein will be apparent to those skilled in the art. Like numbers in the drawings indicate like components throughout the views. As used in the description herein and throughout the claims that follow, unless the context clearly dictates otherwise, the meaning of "a", "an", and "the" includes plural reference, and the meaning of "in" includes "in" and "on". Titles or subtitles can be used herein for the convenience of a reader, which shall have no influence on the scope of the present disclosure.

The terms used herein generally have their ordinary meanings in the art. In the case of conflict, the present document, including any definitions given herein, will prevail. The same thing can be expressed in more than one way. Alternative language and synonyms can be used for any term(s) discussed herein, and no special significance is to be placed upon whether a term is elaborated or discussed herein. A recital of one or more synonyms does not exclude the use of other synonyms. The use of examples anywhere in this specification including examples of any terms is illustrative only, and in no way limits the scope and meaning of the present disclosure or of any exemplified term. Likewise, the present disclosure is not limited to various embodiments given herein. Numbering terms such as "first", "second" or "third" can be used to describe various components, signals or the like, which are for distinguishing one component/signal from another one only, and are not intended to, nor should be construed to impose any substantive limitations on the components, signals or the like.

Figure 2:
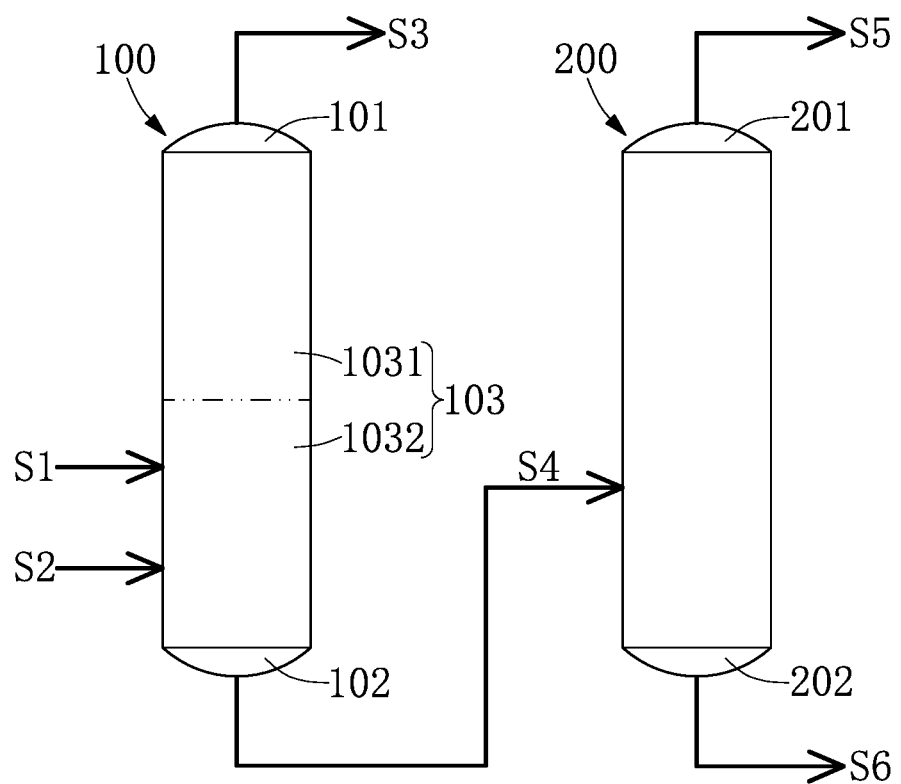
FIG. 2 is a schematic diagram of the unit operations for purifying ethylene glycol according to the embodiment of the present disclosure.

Referring to FIG. 1 and FIG. 2, an embodiment of the present disclosure provides a method for purifying byproduct ethylene glycol of polyester in converting plasticizer, which is a continuous collection method and includes steps of S110, S120, S130, and S140. It should be noted that the order of the steps and the actual way of operation recited in the present embodiment can be adjusted according to requirements and is not limited to those recited in the present embodiment.

The step S110 includes: inputting a reaction liquid waste stream S1 into an ethylene glycol dehydration tower 100 (also called ethylene glycol dehydration column). The reaction liquid waste stream S1 includes ethylene glycol (EG) and 2-ethylhexanol (2-EH).

It should be noted that the reaction liquid waste stream S1 is a liquid waste stream generated in the process of converting polyester (e.g., polyethylene terephthalate, PET) into plasticizer (dioctyl terephthalate, DOTP). More specifically, the process uses polyester waste and raw material 2-ethylhexanol to prepare the plasticizer through a one-step method that combines alcoholysis and transesterification under the action of catalyst. The chemical reaction of the process will generate by-product ethylene glycol. However, the by-product ethylene glycol and the raw material 2-ethylhexanol are azeotropic and difficult to be separated from each other. Accordingly, in the synthesis step of the process, the ethylene glycol can be distilled from the 2-ethylhexanol using a water extraction reaction to produce the reaction liquid waste stream S1 that includes the by-product ethylene glycol and trace amounts of the raw material 2-ethylhexanol.

Since the reaction liquid waste stream S1 includes a relatively high concentration of ethylene glycol, the reaction liquid waste stream S1 has a high COD value (also called chemical oxygen demand), resulting in difficulty in the treatment of the reaction liquid waste stream S1.

Generally, the conventional method for recovering ethylene glycol is to remove water in the reaction liquid waste stream S1 by evaporation to improve the purity of ethylene glycol and accordingly recover the ethylene glycol. However, since the ethylene glycol and the 2-ethylhexanol are azeotropic and difficult to be separated from each other, the purity of ethylene glycol recovered by the conventional method is not high, and the recovered ethylene glycol is difficult to be used as raw material for producing other products, such as raw material for synthetic polyester. In order to solve the above technical problems, the purpose of the present disclosure is to improve the purity of the recovered ethylene glycol through the following steps S120 to S140, so as to enhance the application value of the recovered ethylene glycol.

Further, the ethylene glycol dehydration tower 100 is configured to dehydrate the ethylene glycol in the reaction liquid waste stream S1. The ethylene glycol dehydration tower 100 has a tower top 101, a tower bottom 102, and a tower body 103 located between the tower top 101 and the tower bottom 102. The tower body 103 defines an upper half portion 1031 that is connected to the tower top 101 and a lower half portion 1032 that is connected to the tower bottom 102, and the upper half portion 1031 is connected to the lower half portion 1032. In addition, the tower bottom 102 of the ethylene glycol dehydration tower 100 is heated by a reboiler loop (not shown in the drawings) to provide the heat required for distillation, and the heat source of the reboiler loop is high pressure steam.

In terms of operating parameters of the ethylene glycol dehydration tower 100, a pressure at the tower top 101 of the ethylene glycol dehydration tower 100 is preferably not greater than 1 bar, a reflux ratio of the ethylene glycol dehydration tower 100 is preferably between 0.01 and 3, a temperature at the tower top 101 of the ethylene glycol dehydration tower 100 is preferably between 50° C. and 100° C., and a temperature at the tower bottom 102 of the ethylene glycol dehydration tower 100 is preferably between 80° C. and 160° C., but the present disclosure is not limited thereto.

The step S120 includes: inputting a hot water stream S2 into the ethylene glycol dehydration tower 100 to mix with the reaction liquid waste stream S1 and to remove the 2-ethylhexanol from the reaction liquid waste stream S1 so that the ethylene glycol (EG) is separated from the 2-ethylhexanol (2-EH).

The hot water stream S2 is heated water and is preferably heated pure water. The temperature of the hot water stream S2 is preferably between 40° C. and 95° C., and more preferably between 50° C. and 80° C. In addition, the hot water stream S2 is preferably inputted into the lower half portion 1032 of the ethylene glycol dehydration tower 100, but the present disclosure is not limited thereto.

More specifically, the ethylene glycol is easily miscible with water, but the 2-ethylhexanol is difficultly miscible with water. According to this characteristic, in the present embodiment, the hot water stream S2 within the above temperature range is inputted to the ethylene glycol dehydration tower 100, so that the hot water stream S2 is mixed with the reaction liquid waste stream S1 and is miscible with the ethylene glycol. Moreover, the hot water stream S2 can be used to remove (or exclude) the 2-ethylhexanol from the reaction liquid waste stream S1 since the 2-ethylhexanol is difficultly miscible with water. Therefore, the ethylene glycol and the 2-ethylhexanol in the reaction liquid waste stream S1 can be effectively separated from each other.

According to the above configuration, since the ethylene glycol and the 2-ethylhexanol in the reaction liquid waste stream S1 can be separated from each other more effectively, the azeotropic problem between the ethylene glycol and the 2-ethylhexanol can be effectively improved. Therefore, the ethylene glycol solution S5 obtained in the subsequent step can have a higher purity of ethylene glycol. The organic liquid waste stream S3 obtained in the subsequent step can have a lower COD value since the concentration of ethylene glycol is greatly reduced or even absent, and therefore the organic liquid waste stream S3 can be directly treated by waste treatment.

In an embodiment of the present disclosure, in order to improve the separation efficiency between the ethylene glycol and the 2-ethylhexanol, the reaction liquid waste stream S1 and the hot water stream S2 each have a preferred mass flow rate when being inputted into the ethylene glycol dehydration tower 100. More specifically, the reaction liquid waste stream S1 has a mass flow rate between 300 kg/h and 1,200 kg/h, and preferably between 500 kg/h and 900 kg/h when being inputted into the ethylene glycol dehydration tower 100. The hot water stream S2 has a mass flow rate between 30 kg/h and 600 kg/h, and preferably between 60 kg/h and 420 kg/h when being inputted into the ethylene glycol dehydration tower 100. From another perspective, a mass flow ratio of the reaction liquid waste stream S1 and the hot water stream S2 is between 1:0.1 and 1:0.5, and preferably between 1:0.2 and 1:0.35.

The step S130 includes: dehydrating the ethylene glycol via the ethylene glycol dehydration tower 100 to collect a crude ethylene glycol stream S4 from the tower bottom 102 of the ethylene glycol dehydration tower 100 and to collect an organic liquid waste stream S3 from the tower top 101 of the ethylene glycol dehydration tower 100. The crude ethylene glycol stream S4 includes the ethylene glycol that is dehydrated, and the organic liquid waste stream S3 includes the 2-ethylhexanol.

More specifically, since the ethylene glycol and the 2-ethylhexanol can be more effectively separated from each other through the above step S120, the azeotropic problem between the ethylene glycol and the 2-ethylhexanol has been effectively improved. In addition, the boiling point of ethylene glycol (about 197° C.) is higher than that of 2-ethylhexanol (about 184° C.), and also higher than that of water (about 100° C.). Moreover, 2-ethylhexanol and water can form an azeotropic mixture at a certain ratio, for example, when a content of water in the mixture is 20% (w/w), an azeotropic boiling point of the azeotropic mixture is about 100° C. According to the different boiling points of the different components in the mixture, the ethylene glycol dehydration tower 100 can separate the mixture into a gas phase and a liquid phase by controlling the operating temperature. Further, the substance with a lower boiling point (e.g., the azeotropic mixture including 2-ethylhexanol) will be vaporized and flow toward the tower top 101 of the ethylene glycol dehydration tower 100, and the substance with a higher boiling point (e.g., ethylene glycol) will flow out of the tower bottom 102 of the ethylene glycol dehydration tower 100 in a liquid state, thereby achieving the effect of separating different components in the mixture.

In the present embodiment, the ethylene glycol dehydration tower 100 can dehydrate the ethylene glycol in the reaction liquid waste stream S1, so that the crude ethylene glycol stream S4 is collected from the tower bottom 102 of the ethylene glycol dehydration tower 100. The crude ethylene glycol stream S4 mainly includes the ethylene glycol. The crude ethylene glycol stream S4 does not include any 2-ethylhexanol or includes only a very small amount of 2-ethylhexanol. In other words, since the boiling point of the ethylene glycol is relatively high, the ethylene glycol flows out of the tower bottom 102 in a liquid state.

In addition, the ethylene glycol dehydration tower 100 can vaporize the azeotropic mixture formed by the 2-ethylhexanol and water, and then condense the vaporized vapor through a condenser, so that the organic liquid waste stream S3 is collected from the tower top 101 of the ethylene glycol dehydration tower 100. The organic liquid waste stream S3 includes the 2-ethylhexanol and water. The organic liquid waste stream S3 does not include any ethylene glycol or only includes a small amount of ethylene glycol.

Accordingly, the crude ethylene glycol stream S4 can be provided to the ethylene glycol distillation tower 200 in the subsequent step S140 to continue the purification operation. The organic liquid waste stream S3 can be treated by the subsequent wastewater treatment. It is worth mentioning that since the organic liquid waste stream S3 does not include any ethylene glycol or includes only a very small amount of ethylene glycol, the COD value of the organic liquid waste stream S3 can be effectively reduced, thereby facilitating subsequent wastewater treatment. In an embodiment of the present disclosure, the organic liquid waste stream S3 collected from the tower top 101 of the ethylene glycol dehydration tower 100 preferably has a COD value of not greater than 1,200 mg/L, and more preferably not greater than 1,000 mg/L, but the present disclosure is not limited thereto.

The step S140 includes: inputting the crude ethylene glycol stream S4 into an ethylene glycol distillation tower 200 (also called ethylene glycol distillation column) to collect an ethylene glycol solution S5 from a tower top 201 of the ethylene glycol distillation tower 200 and to collect a high boiling point mixture S6 from a tower bottom 202 of the ethylene glycol distillation tower 200.

The two opposite end portions of the ethylene glycol distillation tower 200 are respectively defined as the tower top 201 and the tower bottom 202. The ethylene glycol distillation tower 200 is configured to purify the crude ethylene glycol stream S4.

More specifically, the crude ethylene glycol stream S4 mainly includes the ethylene glycol, and further includes the high boiling point mixture having the boiling points higher than that of the ethylene glycol, such as propylene glycol, butylene glycol, and other fusel alcohols. Accordingly, the ethylene glycol distillation tower 200 can separate the ethylene glycol and the high boiling point mixture S6 according to different boiling points.

Further, since the boiling point of the ethylene glycol is relatively low in the crude ethylene glycol stream S4, the ethylene glycol can be vaporized in the ethylene glycol distillation tower 200 and flow toward the tower top 201, and then the vaporized ethylene glycol can be condensed through a condenser, so that the ethylene glycol solution S5 with high purity can be collected at the tower top 201 of the ethylene glycol distillation tower 200.

In an embodiment of the present disclosure, the ethylene glycol solution S5 preferably has an ethylene glycol purity of not less than 90%, and more preferably not less than 95%. It is worth mentioning that since the recovered ethylene glycol has a relatively high purity of ethylene glycol, the recovered ethylene glycol can be further used as the raw material for production of other products, such as synthetic polyester, thereby enhancing the application value of the recovered ethylene glycol.

In addition, since the boiling point of the high boiling point mixture S6 is relatively high in the crude ethylene glycol stream S4, the high boiling point mixture S6 flows out of the tower bottom 202 in a liquid state. It is worth mentioning that the high boiling point mixture S6 has a calorific value, and the calorific value is preferably not less than 1,500 kcal/kg. In other words, the high boiling point mixture S6 can be directly incinerated without causing pollution.

In terms of operating parameters of the ethylene glycol distillation tower 200, a pressure at the tower top 201 of the ethylene glycol distillation tower 200 is preferably not greater than 1 bar, a reflux ratio of the ethylene glycol distillation tower 200 is preferably between 0.01 and 10, a temperature at the tower top 201 of the ethylene glycol distillation tower 200 is preferably between 120° C. and 150° C., and a temperature at the tower bottom 202 of the ethylene glycol distillation tower 200 is preferably between 130° C. and 170° C., but the present disclosure is not limited thereto.

Since the ethylene glycol solution S5 collected by the method of the present embodiment has the high ethylene glycol purity, the ethylene glycol solution S5 has high application value. Since the organic liquid waste stream S3 collected by the method of the present embodiment has a low COD value, the organic liquid waste stream S3 can be directly treated by wastewater treatment. Furthermore, since the high boiling point mixture S6 collected by the method of the present embodiment has an incineration recoverable calorific value, the high boiling point mixture S6 can be directly incinerated. In other words, the method for purifying ethylene glycol of the present embodiment enables the recovered ethylene glycol solution S5 to have high purity, and thus has high application value. In addition, the waste generated in the method can be directly treated without causing serious pollution to the environment.

In conclusion, by virtue of "(2) inputting a hot water stream into the ethylene glycol dehydration tower to mix with the reaction liquid waste stream and to remove the 2-ethylhexanol from the reaction liquid waste stream so that the ethylene glycol is separated from the 2-ethylhexanol; in which the hot water stream is heated water, and a temperature of the hot water stream is between 40° C. and 95° C.", "(3) dehydrating the ethylene glycol via the ethylene glycol dehydration tower to collect a crude ethylene glycol stream from a tower bottom of the ethylene glycol dehydration tower and to collect an organic liquid waste stream from a tower top of the ethylene glycol dehydration tower; in which the crude ethylene glycol stream includes the ethylene glycol that is dehydrated, and the organic liquid waste stream includes the 2-ethylhexanol", and "(4) inputting the crude ethylene glycol stream into an ethylene glycol distillation tower to collect an ethylene glycol solution from a tower top of the ethylene glycol distillation tower", the recovered ethylene glycol solution has high purity, and thus has high application value. Moreover, the waste (e.g., organic liquid waste stream or high boiling point mixture) generated in the method of the present disclosure can be directly treated by wastewater treatment or incineration, which will not cause serious pollution to the environment.

The foregoing description of the exemplary embodiments of the disclosure has been presented only for the purposes of illustration and description and is not intended to be exhaustive or to limit the disclosure to the precise forms disclosed. Many modifications and variations are possible in light of the above teaching.

The embodiments were chosen and described to explain the principles of the disclosure and their practical application so as to enable others skilled in the art to utilize the disclosure and various embodiments and with various modifications as are suited to the particular use contemplated. Alternative embodiments will become apparent to those skilled in the art to which the present disclosure pertains without departing from its spirit and scope.

What is claimed is:

1. A method for purifying by-product ethylene glycol which is a continuous collection method and comprises the following steps (1) to (4):
   (1) inputting a reaction liquid waste stream into an ethylene glycol dehydration tower; wherein the reaction liquid waste stream is generated in a process of converting polyester into plasticizer, the reaction liquid waste stream includes ethylene glycol and 2-ethylhexanol, and the reaction liquid waste stream has a mass flow rate between 300 kg/h and 1,200 kg/h when the reaction liquid waste stream is inputted into the ethylene glycol dehydration tower;
   (2) inputting a hot water stream into the ethylene glycol dehydration tower to mix with the reaction liquid waste stream and to remove the 2-ethylhexanol from the reaction liquid waste stream so that the ethylene glycol is separated from the 2-ethylhexanol; wherein the hot water stream is heated water, and a temperature of the hot water stream is between 40° C. and 95° C., the hot water stream is inputted into the ethylene glycol dehydration tower at a lower level than the reaction liquid waste stream, the hot water stream has a mass flow rate between 30 kg/h and 600 kg/h when the hot water stream is inputted into the ethylene glycol dehydration tower; and a mass flow ratio of the reaction liquid waste stream to the hot water stream is between 1:0.1 and 1:0.5;
   (3) dehydrating the ethylene glycol via the ethylene glycol dehydration tower to collect a crude ethylene glycol stream from a tower bottom of the ethylene glycol dehydration tower and to collect an organic liquid waste stream from a tower top of the ethylene glycol dehydration tower; wherein the crude ethylene glycol stream includes the ethylene glycol that is dehydrated, the organic liquid waste stream includes the 2-ethylhexanol, and the organic liquid waste stream has a chemical oxygen demand (COD) value of not greater than 1,200 mg/L; and
   (4) inputting the crude ethylene glycol stream into an ethylene glycol distillation tower to collect an ethylene glycol solution from a tower top of the ethylene glycol distillation tower.

2. The method according to claim 1, wherein in the step (2), the temperature of the hot water stream is between 50° C. and 80° C.

3. The method according to claim 1, wherein in the step (2), the hot water stream is inputted into a lower half portion of the ethylene glycol dehydration tower.

4. The method according to claim 1, wherein in the step (4), the ethylene glycol solution collected from the tower top of the ethylene glycol distillation tower has an ethylene glycol purity of not less than 90%.

5. The method according to claim 1, wherein the step (4) further includes: collecting a high boiling point mixture from a tower bottom of the ethylene glycol distillation tower.

6. The method according to claim 5, wherein in the step (4), the high boiling point mixture collected from the tower bottom of the ethylene glycol distillation tower has a calorific value of not less than 1,500 kcal/kg.

7. The method according to claim 1, wherein the tower bottom of the ethylene glycol dehydration tower is heated by a reboiler loop to provide the heat required for distillation, and the heat source of the reboiler loop is high pressure steam.

8. The method according to claim 1, wherein a pressure at the tower top of the ethylene glycol dehydration tower is not greater than 1 bar, a reflux ratio of the ethylene glycol dehydration tower is between 0.01 and 3, a temperature at the tower top of the ethylene glycol dehydration tower is between 50° C. and 100° C., and a temperature at the tower bottom of the ethylene glycol dehydration tower is between 80° C. and 160° C.

9. The method according to claim 1, wherein a pressure at the tower top of the ethylene glycol distillation tower is not greater than 1 bar, a reflux ratio of the ethylene glycol distillation tower is between 0.01 and 10, a temperature at the tower top of the ethylene glycol distillation tower is between 120° C. and 150° C., and a temperature at the tower bottom of the ethylene glycol distillation tower is between 130° C. and 170° C.

* * * * *